United States Patent [19]

Teodorescu et al.

[11] 4,223,005
[45] Sep. 16, 1980

[54] ANTIBODY COATED BACTERIA

[75] Inventors: Marius C. Teodorescu, Oak Park; Eugene P. Mayer; Sheldon Dray, both of Chicago, all of Ill.

[73] Assignee: University of Illinois Foundation, Urbana, Ill.

[21] Appl. No.: 12,326

[22] Filed: Feb. 15, 1979

Related U.S. Application Data

[63] Continuation of Ser. No. 637,319, Dec. 3, 1975, abandoned.

[51] Int. Cl.$^3$ ............... G01N 33/48; G01N 33/50; G01N 33/54
[52] U.S. Cl. ............................. 424/12; 23/230 B; 424/3; 424/85; 424/88; 435/7
[58] Field of Search ............... 424/3, 8, 12, 13, 85, 424/88; 23/230 B; 435/7

[56] References Cited

U.S. PATENT DOCUMENTS

| | | | |
|---|---|---|---|
| 3,553,310 | 1/1971 | Csizmas | 424/8 X |
| 3,639,558 | 2/1972 | Csizmas | 424/12 |
| 3,873,684 | 3/1975 | Fujita | 424/12 |
| 3,882,225 | 5/1975 | Patel | 424/12 |
| 3,925,018 | 12/1975 | Saunders | 23/230 B |

OTHER PUBLICATIONS

Molinaro, The J. of Immunol. vol. 114, No. 2, Pt. 1, Feb. 1975, pp. 908–910.
Molinaro, Nature, vol. 248, Apr. 5, 1974, pp. 515–517.
Zaalberg, Nature, vol. 202, Jun. 20, 1964, p. 1231.
Roitt, Essential Immunol., Blackwell Sci, Pub. London 2nd Ed. 2nd Print., 1974 pp. 43–49, 55–68.

*Primary Examiner*—Anna P. Fagelson
*Attorney, Agent, or Firm*—Merriam, Marshall & Bicknell

[57] ABSTRACT

Process for identification and enumeration of B and T lymphocytes in an unseparated peripheral body sample comprises contacting the sample with two morphologically distinguishable bacteria, each of which is coated with an antibody specific to an antigen on one of the B or T cells. The presence of a B or a T cell is determined by rosette formation with the corresponding bacteria, as viewed under a microscope in a smear.

12 Claims, No Drawings

ANTIBODY COATED BACTERIA

The invention described herein was made, in part, in the course of work under grants from the Department of Health, Education, and Welfare.

This is a continuation of application Ser. No. 637,319, filed Dec. 3, 1975 now abandoned.

This invention relates to a composition and a method for identifying and counting morphologically indistinguishable blood or other cells bearing different antigens and for counting the relative numbers of such cells in a smear or suspension. More particularly, the invention relates to a composition and method for the identification of lymphocyte sub-populations in blood samples, by labeling the cells with morphologically distinguishable bacteria coated with purified antibody specific to the antigens carried by the lymphocytes.

BACKGROUND

It is known that lymphocytes, which appear as a unique population of cells in the peripheral blood of animals, including man, contain two functionally different sub-populations of cells known as T cells and B cells. In view of indications that the relative concentrations of the B and T cells may serve as indicators of certain physiological or pathological conditions in the body of the animal, many attempts have been made to develop a method for obtaining differential counts of the T and B cells in a blood sample. These attempts have been complicated by the fact that B and T cells cannot be distinguished on the basis of their morphology.

As present, the most widely used methods for enumerating the sub-populations of T cells and B cells in blood samples are based on immunofluorescence and rosette formation with erythrocytes. These methods require the preparation of purified suspensions of lymphocytes by methods which are laborious and which usually cause a loss in a particular sub-population of cells. In addition, the morphology of the cells counted as T or as B cells can be determined only with difficulty on stained preparations. Further, these methods permit counting only one type of cell at a time, i.e., either T cells or B cells, but not both simultaneously.

More recent methods for simultaneous identification of T and B cells in leucocyte suspensions use fluorescent antibody of two different colors, e.g., fluorescein and rhodamine, but the use of these procedures as routine tests is precluded by the difficulty, the special equipment, and the extensive training of the operator which they entail.

The use of bacteria to identify some lymphocytes in suspension is known. For example, *staphylococcus aureus*, strain Cowan I is known to bind to cells bearing IgG, a class of immunoglobulins present on only some B cells. The use of this bacteria does not therefore afford a means of distinguishing between B and T lymphocytes

SUMMARY OF THE INVENTION

The present invention provides a simple, reproducible and easily standarizable method for simultaneous identification of lymphocyte sub-populations in stained blood smears, based on the ability of antibody coated bacteria to bind to a particular lymphocyte sub-population. The sub-populations of lymphocytes, while morphologically indistinguishable, are characterized by bearing different antigens on the membrane, B cells having surface immunoglobulin and T cells having thymus cell antigens.

In accordance with the invention, morphologically distinguishable bacteria are coated with purified antibodies specific to the antigens contained on the membranes of the lymphocytes and brought into contact with the cells of the blood sample to be analyzed. A bacteria coated with purified antibody against the surface immunoglobulin of B cells binds to B cells when brought in contact therewith, the bound bacteria serving as markers which are visible on observation under a microscope. The presence and number of T cells can similarly be determined by using a different type of bacteria coated with an antibody which causes the bacteria to bind to the T cells. Since it is at present technically difficult to prepare a purified anti-thymus cell antibody, an indirect method analogous to that used for immunofluorescence or rosette formation can be employed. In accordance with this procedure, a specific anti-thymus cell anti-serum is prepared in a heterologous host and the lymphocyte cell population treated in the cold with this antiserum. Subsequently, the cells which bound antibody (immunoglobulin molecules) are able to bind bacteria coated with purified anti-immunoglobulin antibody. By selecting two or more different bacteria which are morphologically distinguishable and which are compatible, i.e., do not interact when coated with the appropriate antibody, the presence and relative number and B and T cells in a stained blood smear can be determined by the association therewith of the different bacteria.

Briefly summarized, the method of the invention involves selecting at least two distinguishable bacteria; selecting suitable antibodies capable of binding the bacteria to the different cells to be identified and enumerated and coating the bacteria with suitable preparations of purified antibodies; contacting the blood sample with both of the antibody coated bacteria; and enumerating each different type of cell by the presence of one of the bacteria bound to its surface. These aspects of the invention will be considered in detail below.

DETAILED DESCRIPTION

Selection of Bacteria

For use in the invention, both the size and shape of the bacteria are important. The bacteria must be small enough relative to the size of the cells which are to be counted to permit a sufficient number of bacteria to bind to the cells to permit identification, but at the same time the bacteria cannot be so small so as not to be easily visible under a microscope. For use in the invention, bacteria having a longest dimension within the range of about 0.2 to 2 microns are generally useful.

With respect to shape, bacterial useful in the invention should be readily distinguishable on examination so as to permit clear differentiation between cells bound with bacteria of one shape, indicating one type of cell, such as a B cell, from those bound by bacteria of a different shape, indicating a different cell, e.g., a T cell. Examples of preferred pairs of bacteria useful for determining B and T cells comprise *E.coli* (bacilli) and *G.tetragenus* (cocci) for the rabbit and *E.coli* and *Streptococus lactis* (cocci) for man. These bacteria have appopriate sizes for use in the invention, and have readily distinguishable shapes. In addition, the uncoated bacteria do not bind to lymphocytes. Bacteria which can be used in the invention, include *Staphylococcus aureus*, and others.

Bacteria useful in the invention must not bind with lymphocytes prior to coating with the antibody. A further requirement for the bacteria which can be used in the invention is the ability to accept a coating of antibody sufficient to cause the coated bacteria to bind firmly on the lymphocyte membrane of the cells having a particular antigen. While the ability of a particular bacteria to receive sufficient antibody for this purpose cannot be predicted, a simple screening process can be used to establish its suitability. For such screening, the bacteria is coated with antibody corresponding to the antigen carried by the cell and brought into contact with a solution containing antigen in a concentration less than about 0.1 µg/ml. If the antibody coated bacteria agglutinate to an extent visible under a microscope, the test is positive, and the bacteria can be used in the method of the invention.

In addition to having the ability to hold sufficient antibody, the bacteria used for simultaneous identification of two different cells, such as B and T cells, must not take part in any inactivating interactions between the bacteria and a particular purified antibody. While it is also impossible to predict such interactions, their existence or absence can be readily determined experimentally by one skilled in the art.

Selection of Antibodies

The invention depends for its results on the binding of bacteria to the surface of a lymphocyte or other cell by reason of the interaction between an antibody which coats the bacteria and the corresponding antigen found on the membrane of the cell. When using a mixture of different bacteria for simultaneous identification of different cells, such as T and B cells, in the same suspension or smear, the two antibody preparations should be compatible, i.e., the bacteria should be coated with antibodies which do not interact. For example, for the identification of human lymphocytes for clinical use, it is useful to prepare antibodies by means of rabbits of particular allotypes. Anti-human κ and λ light chains are prepared by inoculation of κ or λ chains (Bence Jones proteins) into rabbits homozygous for the b5 allotype of κ light chain. The anti-T cell antiserum is made in rabbits homozygous for the b4 allotype and the indirect reagent, anti-b4 allotype antibody, is made in b5 homozygous rabbits. Thus, on the bacteria, there will be only b5 molecules directed against other components in the system. As a further example, for use in analyzing rabbit blood lymphocytes, bacteria are coated with b4 Ig molecules having anti-b5 activity and b4 Ig molecules having anti-guinea pig Ig activity. Since the b5 allotype is not present on guinea pig immunoglobulins, all the reagents in the system are compatible. In a similar manner, one skilled in the art can select antibodies for use in the invention which are compatible under any given circumstances.

Coating the Bacteria

Intact antibody, fragments thereof (monovalent Fab and bivalent F(ab)2) or hybrid antibodies can be used to coat the bacteria for use in the invention. Antiserum against immunoglobulins is produced in conventional fashion in heterologous or homologous hosts. A purified fraction of antibody specific only for immunoglobulins is prepared in conventional fashion using an immunoadsorbent column. In the purification process, an antigen, which can be, for example, the immunoglobulin found on B cells or the heterologous immunoglobulin bound on T cells by prior treatment with anti-thymus cell antibody, is bound to cyanogen bromide-activated sepharose columns, the antiserum is passed through the column and the antibody which is bound to the antigen is eluted. The eluted fraction comprises the purified antibodies which are coated on the bacteria.

Any known method of causing the antibodies to chemically bind on the bacteria can be used. A particularly preferred reagent for this purpose is glutaraldehyde. To coat the bacteria, a bacterial suspension in saline is first fixed with glutaraldehyde, washed and then incubated with the purified antibody preparation. Any large clumps which are present in the resulting bacterial suspension are removed, as by sonication. The antibody coated bacteria are then washed and adjusted to a desired bacterial cell density.

Treating Cells with Antibody Coated Bacteria

After washing, the cells to be identified and enumerated are brought into contact with the antibody-coated bacteria. In this aspect of the process of the invention, we have found it advisable to use a ratio of about 100–200 bacteria for each cell, and to centrifuge the mixture at 900 xg for about 5–10 minutes, during which time the antibody coated bacteria are bound to the surface of the cells bearing the antigen specific to the antibody. The cells are then resuspended by vigorous pipetting and the number of cells having bacteria attached is counted in a wet mount under a phase contrast microscope.

The immunoglobulins on the surface of the cells can be either their normal constituents or antibody bound to particular surface antigens. When the immunoglobulins are not the normal constituents of the cell surface, the suspension is prepared in advance according to the known procedure used for indirect (sandwich) immunofluorescence (David et al., "Microbiology", pp. 397–399, 451–453, Harper and Row, 1973) or for indirect rosette formation with antibody coated erythrocytes (Strelkauskas et al., *Clin. Exp. Immunol.*, 22, 62, 1975). The cells are treated with specific antiserum against the antigen to be determined, washed and the antibody molecules on the cell surface detected by bacteria coated with purified antibody prepared against the heterologous immunoglobulins having the selected antibody activity.

As applied to the detection and enumeration of B and T lymphocytes on stained preparations in accordance with the invention, the following procedure is employed. A washed whole blood (0.1–0.2 ml) cell suspension is mixed with 0.2–0.3 ml of antibody coated bacteria in 0.5% albumin in saline at an optimal ratio of about 1–2 bacterial cells for each blood cell (white and red blood cells included) and centrifuged together at 900 xg for six minutes to promote binding. From these proportions of reactants, it would be expected that the ratio of bacteria to blood cells, including the red cells (which have almost the same size as lymphocytes) would be very low, making it difficult to differentiate between labeled and unlabeled cells in the blood smears. Unexpectedly, however, it was found that the use of about one bacterial cell for each blood cell, white and red included, is sufficient to obtain 4–20 bacteria on each labeled lymphocyte. It is probable that during centrifugation the red cells, being heavier, sediment first, permitting the leukocytes to react more readily with the bacteria at a high operational ratio.

When the treated blood cells are remixed, smeared and examined under a microscope, the background contains few unbound bacteria scattered throughout the field compared to the localized association of several bacteria with each of the specific leukocytes, making them very easy to recognize and count.

For simultaneous identification of different cells, the blood is mixed with morphologically different kinds of antibody coated bacteria and the procedure described above is followed. On smears it is then possible to identify if a particular antigen and surface Ig are on different cells. Compared to the regular blood smears, treatment with antibody coated bacteria offers the advantage of displaying, in addition to other leukocytes, the two subpopulations of lymphocytes, T and B cells, as different cells, even though morphologically T and B cells are indistinguishable. For other uses, cells having two different antigenic markers on the same cells can be detected using the method of the invention.

The invention is illustrated by the following example, in which the percentage and actual number of B and T cells in rabbit lymph node cell suspension and in rabbit peripheral blood were determined.

EXAMPLE

Preparation of purified antibody

Essentially, the procedure of Axen and Ernback (Eur. J. Biochem. 18, 351) was used. An immunoadsorbent column of Sepharose-conjugated rabbit b5-IgG was equilibrated with borate buffered saline. Anti-b5 antiserum prepared in b4 rabbits was passed through the column. The column was washed with saline borate buffer (0.13 M NaCl, 0.16 M boric acid, pH 8.0) and the bound antibody eluted with 0.1 M glycine sulfate buffer (pH 2.3). The pH of the eluate was quickly adjusted to pH 7-8 with 1M Tris (tris-hydroxymethyl-aminomethane) to prevent the denaturation of the eluted antibody. The eluate was concentrated by ultrafilitration, dialysed against saline and the antibody concentration adjusted to 1 mg/ml ($A_{280}$ 1 mg/ml = 1.5).

Preparation of bacteria and coating with purified antibody

*Escherichia coli* (a small bacillus) grown at 37° C. in Difco antibiotic medium III under continuous aeration for 24 hours, was washed with saline 3 times and stored at −20° C. until used. *Gaffkya tetragenus* (a large coccus) was grown and stored under the same conditions.

Coating bacteria with purified antibody

The bacteria were suspended in saline to give an O.D. at 600 nm of 150 for *E. coli* and 300 for *G. tetragenus* approximately $5 \times 10^{10}$ cells/ml). To each ml of bacterial suspension was added 5 ml of saline, 1 ml of 0.015 M phosphate buffer pH 8.0 and 1.5 ml of a 25% glutaraldehyde solution neutralized with 10% $Na_2CO_3$. The suspension was incubated at 4° C. for 18 hr with vigorous and continuous stirring. The cells were harvested and washed 3 times with saline by centrifugation at 5000 xg for 10 minutes. Approximately $2-5 \times 10^{10}$ bacteria were suspended in 1 ml of 0.015 M phosphate buffer pH 6.0 and 1 ml of purified antibody (1 mg/ml) was added. The mixture was incubated at 50° C. for 1 hr and the coated cells were harvested by centrifugation and suspended in 5 ml of saline. The suspension was sonicated with a model W185D sonicator (Heat Systems, Ultrasonics, Inc.) at 60 watts for 1 minute in the cold to dispose clumps of bacteria. The suspension was washed 3 times with saline by centrifugation at 5000 xg for 10 minutes. The same procedure was used to coat bacteria with purified rabbit anti-guinea pig antibody. The immunosorbent column contained guinea pig IgG and the antiserum was prepared by inoculating rabbits homozygous for the b4 allotype with guinea pig IgG. The purified antibody was therefore specific for guinea pig IgG and had the b4 kappa chain allotype.

Preparation of anti-Thymus cells antiserum

Essentially the method described by Strelkauskas et al. (*Clin. Exp. Immunol.*, 22, 62 (9175)) was used. Thymus cells ($10^8$) were inoculated i.p. in guinea pigs and boostered 3 weeks later with the same amount also i.p. One week later guinea pig serum was harvested and adsorbed with v/v packed erythrocytes, liver cells and bone marrow cells.

Labeling lymph node cells with antibody coated bacteria

A suspension of lymph node cells from homozygous rabbits was prepared by pressing the lymp nodes through a stainless steel screen and filtering the suspension through a cotton wool column to remove clumps. The suspension was washed in the cold with Eagle's MEM and adjusted to $2 \times 10^6$ cells/ml in MEM containing 0.1% bovine serum albumin. Then 0.2 ml of suspension was mixed with anti-b5 coated bacteria (either *E. coli* or *G. tetragenus* in 0.1 ml) at a ratio of 100-200 bacteria for each lymphocyte. The mixture was centrifuged at 900 xg for 5 minutes in a swinging bucket type centrifuge and the cells resuspended by vigorous pipetting. The suspension was prepared in a wet mount and the cells with and without attached bacteria counted under a phase contrast microscope. As a control, an identical aliquot was prepared using bacteria coated with a wrong anti-allotype, namely anti-b4 allotype. Bacteria coated with anti-b5 allotype purified antibody surrounded 45-48% of the cells in the lymph node cell suspension while less than 2% of the cells were bound by the bacteria coated with anti-b4 antibody.

In order to identify thymus cell antigen on lymph node cells the cell suspension was first treated with anti-T cell antiserum for 1 hr at 0° C. and washed 3 times to remove the excess antiserum. As a control, a suspension not treated with guinea pig antiserum was used. The cells were then treated with anti-guinea pig IgG coated bacteria (either *E. coli* or *G. tetragenus*) and counted under a phase contrast microscope. About 45-51% of the cells were found to be surrounded by bacteria.

Identification of B and T cells in blood smears

Blood was obtained from the marginal ear vein on heparin (100 μ/ml of blood) from b5 homozygous rabbits. The blood was washed 4 times with MEM containing 0.1% albumin and 0.01% sodium azide by centrifugation at 900 xg for 5 minutes. To 1 ml reconstituted blood, 10 μl of guinea pig anti-rabbit thymus cell antiserum was added and incubated 1 hour at 0° C. The blood cells were washed again three times. To 0.1 ml of blood, 0.1 ml of antibody coated bacterial suspension was added and centrifuged at 900 xg for 6 minutes. The excess fluid was removed and a large drop of the blood cell suspension, approximately at the concentration of the blood was placed on a clean slide, which is then inverted and vigorously shaken to spread the blood as a smear. This procedure for preparing the smear is advantageous in that it prevents destruction of the cells which occurs if any mechanical means of spreading the sample into a smear is used. As an alternative, the smear can be prepared by use of a cyto-centrifuge. Sample smears were then stained with Wright's stain and examined under oil immersion.

As may be seen in Table 1, 46-51% of the lymphocytes had associated bacteria coated with anti-b5 antibody; whether E. coli or G. tetragenus was used, the same percentages were obtained. When the blood was treated with anti-thymus cell antiserum 43-46% of the cells were surrounded by bacteria coated with purified anti-guinea pig antibody indicating that they had thymus cell antigens. Simultaneous use of E. coli coated with anti-b5 and of G. tetragenus coated with anti-guinea pig antibody showed 51% E. coli labeled lymphocytes, 43% G. tetragenus coated lymphocytes and the remaining 6% coated with no bacteria. This percentage of unlabeled cells was expected since cells are present bearing lambda light chain allotypes for which no specific antibody coated bacteria were prepared. The same percentages of cells bearing b5 allotype and thymus cells antigens were found when E. coli was coated with anti-guinea pig antibody and G. tetragenus was coated with anti-b5 antibody (See Table 1). No cell with lymphocyte morphology was found having both kinds of bacteria at the same time although occasionally monocytes doubly labeled were seen. All controls were negative, i.e., no lymphocyte could be identified as being labeled with bacteria if anti-b4 coated bacteria were used or when blood untreated with guinea pig antiserum was treated with bacteria coated with anti-guinea pig antibody.

TABLE I

Identification of lymphocytes bearing thymus cell antigen (T cells) or b5-Ig (B cells) amone lymphocytes from a b5-homozygous rabbit by observing the association of antibody coated bacteria with T or B cells on stained blood smears.

| Pretreatment with GP* anti-T antibody | Antibody Coated Bacteria Purified antibody - Bacteria | % Lymphocytes labeled with G. tetragenus | %Lymphocytes labeled with E. coli |
|---|---|---|---|
| No | anti-b5 Ig - E. coli | — | 49 |
| No | anti-b4 Ig - E. coli | — | 0 |
| No | anti-b5 Ig - G. tetragenus | 51 | — |
| No | anti-b4 Ig - G. tetragenus | 0 | — |
| Yes | anti-GP Ig - E. coli | — | 48 |
| Yes | anti-GP Ig - G. tetragenus | 46 | — |
| No | anti-GP Ig - E. coli | — | 1 |
| No | anti-GP Ig - G. tetragenus | 0 | — |
| Yes | anti-b5 Ig - G. tetragenus anti-GP Ig - E. coli | 48 | 43 |
| Yes | anti-GP Ig - G. tetragenus anti-b5 Ig - E. coli | 43 | 51 |
| No | anti-GP Ig - G. tetragenus anti-b5 Ig - E. coli | 1 | 49 |

*Guinea Pig

The foregoing detailed description has been given for clearness of understanding only, and no unnecessary limitations should be understood therefrom, as modifications will be obvious to those skilled in the art.

What is claimed is:

1. A method for identification and enumeration of a subpopulation of lymphocytes in an unseparated peripheral blood sample, said subpopulation bearing a characteristic antigen on the membrane of its cells, which method comprises contacting said sample with a bacteria having no natural affinity for said subpopulation, said bacteria being coated with antibody directed against said antigen, whereby said bacteria binds only with said cell subpopulation, preparing a smear of said sample, and identifying and counting said subpopulation of lymphocytes in said smear by noting the presence of said bacteria bound to the cells thereof.

2. A method for identification and enumeration of at least two different subpopulations of lymphocytes in an unseparated peripheral blood sample, each subpopulation bearing a different characteristic antigen on the membrane of its cells, which method comprises contacting said sample with at least two morphologically distinguishable types of bacteria, each of said types being coated with compatible antibody directed against a different one of said antigens, whereby each type of bacteria binds only with a specific cell subpopulation, preparing a smear of said sample, and identifying and counting each subpopulation of lymphocytes in said smear by noting the presence of one of said bacteria bound to the cells thereof.

3. The method of claim 2 in which at least one of said bacteria is a coccus and at least one is a bacillus.

4. The method of claim 3 wherein said bacteria are selected from the group consisting of *Escherichia coli, Gaffkya tetragenus, Staphylococcus aureus,* and *Streptococcus lactis.*

5. The method of claim 2 wherein said bacteria have a longest dimension within the range of about 0.2-2 microns.

6. The method of claim 2 wherein said cell subpopulations are T lymphocytes and B lymphocytes in a peripheral blood sample and said method includes the steps of washing the total blood cells, treating the cells with a heterologous anti-thymus cell antiserum, adding to the sample a mixture of two morphologically distinguishable bacteria, one of which is chemically coated with antibody specific to the immunoglobulin present on the B cells and the other of which is chemically coated with antibody specific to the heterologous immunoglobulins present on said T cells as a result of said treatment with anti-thymus cell antiserum, collecting the cells from said sample, preparing a smear with said cells, staining said smear, and counting in the stained smear the lymphocytes associated with each of said bacteria.

7. The method of claim 6 wherein said bacteria are added to said sample in a ratio of about 0.05-5 bacterial cells for each blood cell in said sample and the mixture is centrifuged at at least 900 xg for at least about 5 minutes.

8. The method of claim 7 in which said smear is prepared by producing a suspension of said cells, placing a drop of said suspension on a slide, inverting the slide and shaking to spread said drop into a smear.

9. A composition for use in simultaneous identification and enumeration of B lymphocytes and T lymphocytes in the peripheral blood of an animal, which composition comprises a mixture of two morphologically distinguishable types of bacteria having no natural affinity for either of said lymphocytes, one of said types of bacteria being chemically coated with an antibody specific to an antigen associated with B lymphocytes and the other of said types being chemically coated with an antibody specific to an antigen associated with T lymphocytes, the quantity of antibody in said coating being sufficient to cause the bacteria to bind to a lymphocyte bearing the corresponding antigen.

10. The composition of claim 9 wherein said bacteria have a longest dimension within the range of about 0.2–2 microns.

11. The composition of claim 9 wherein at least one of said bacteria is a coccus and at least one is a bacillus.

12. The composition of claim 11, wherein said bacteria are selected from the group consisting of *Escherichia coli, Gaffkya tetragenus, Staphylococcus aureus* and *Streptococcus lactis.*

* * * * *

UNITED STATES PATENT AND TRADEMARK OFFICE
CERTIFICATE OF CORRECTION

PATENT NO. : 4,223,005

DATED : September 16, 1980

INVENTOR(S) : TEODORESCU ET AL.

It is certified that error appears in the above-identified patent and that said Letters Patent are hereby corrected as shown below:

Abstract, line 2, "body" should be --blood--.

Col. 6, line 12,, "9175", should be --1975--.

Col. 7, line 37, "amone", should be --among--.

Col. 8, line 47, (Claim 7), "0.05", should be --0.5--.

Signed and Sealed this

Third Day of February 1981

[SEAL]

Attest:

RENE D. TEGTMEYER

Attesting Officer   Acting Commissioner of Patents and Trademarks